United States Patent [19]
Wright et al.

[11] Patent Number: 6,123,904
[45] Date of Patent: Sep. 26, 2000

[54] WATER IMPURITY ANALYZER

[75] Inventors: Paul George Wright, Pleasant Dale, Nebr.; Curtis W. Nicholls, Kingwood, Tex.; Clifford LaRue McDonald, Jr., Lincoln, Nebr.

[73] Assignee: Isco, Inc., Lincoln, Nebr.

[21] Appl. No.: 09/049,629

[22] Filed: Mar. 27, 1998

Related U.S. Application Data

[62] Division of application No. 08/634,007, Apr. 15, 1996, Pat. No. 5,733,789, which is a division of application No. 08/386,699, Feb. 10, 1995, Pat. No. 5,531,961.

[51] Int. Cl.[7] .................................................. G01N 27/08
[52] U.S. Cl. ............................ 422/80; 422/117; 436/146
[58] Field of Search ................................... 422/105, 106, 422/110, 111, 79, 80, 117; 340/608; 436/146

[56] References Cited

U.S. PATENT DOCUMENTS

| | | | |
|---|---|---|---|
| 4,167,858 | 9/1979 | Kojima et al. | 340/608 |
| 4,277,438 | 7/1981 | Ejzak et al. | |
| 4,311,047 | 1/1982 | Hubbard, Jr. et al. | 340/608 |
| 4,630,036 | 12/1986 | Ford | 340/608 |
| 4,642,614 | 2/1987 | Cook | 340/608 |
| 4,647,919 | 3/1987 | Wright et al. | 340/608 |
| 5,141,717 | 8/1992 | McRae. | |

FOREIGN PATENT DOCUMENTS

| | | |
|---|---|---|
| 0 202 820 A2 | 5/1986 | European Pat. Off.. |
| 0 256 684 A2 | 7/1987 | European Pat. Off.. |
| 0 498 888 A1 | 11/1990 | European Pat. Off.. |
| 2 165 360A | 10/1985 | United Kingdom. |
| WO 88/06730 | 9/1988 | WIPO. |

Primary Examiner—Jeffrey Snay
Attorney, Agent, or Firm—Vincent L. Carney

[57] ABSTRACT

To determine the total organic carbon content of a flowing liquid in a continuous process, water and oxidizing agents enter lower ports in a multi-stage column and flow upwardly through residence chambers as they are mixed. Spaced apart along the upper path of the liquid, there are helical reaction grooves relatively shallow and containing at least one helical groove to cause rapid motion of the liquid. An ultraviolet lamp extends downwardly through the center of the column so that the outer confining surface of the helical grooves is the outer surface of the ultraviolet lamp, causing the liquid to move rapidly in intimate contact with the ultraviolet lamp to receive intense radiation. The stages are separate and interchangeable so that selected sizes may interconnect. The residence chambers may have different sizes to permit different lengths of residence time and thus permit tailoring of the reaction to the expected organic carbon content and possible side reactions with other impurities in the water.

2 Claims, 7 Drawing Sheets

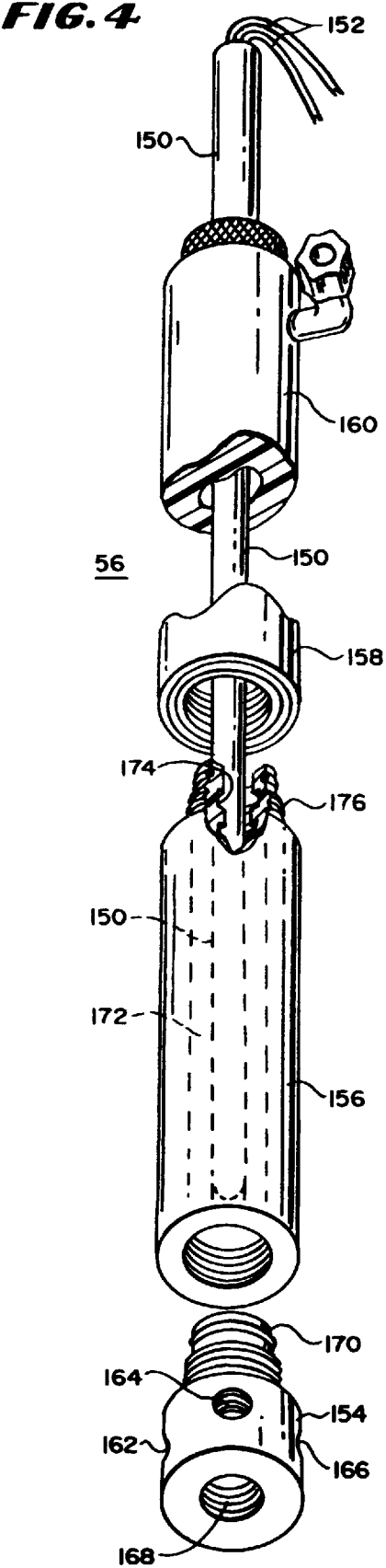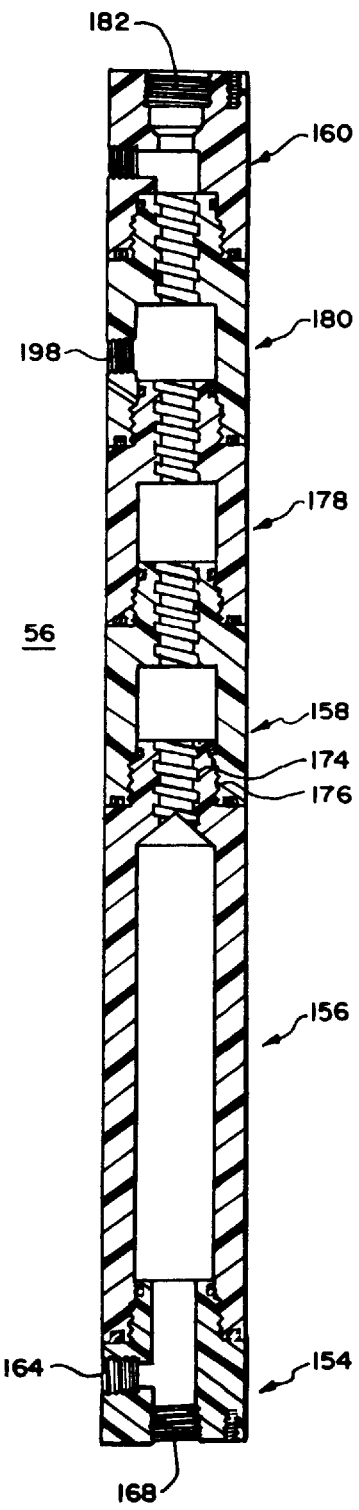

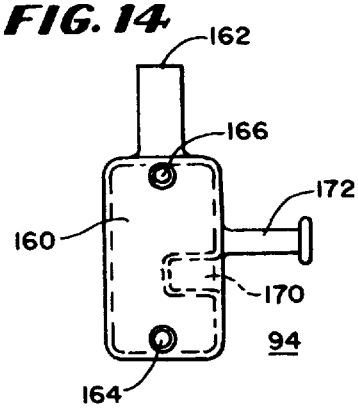
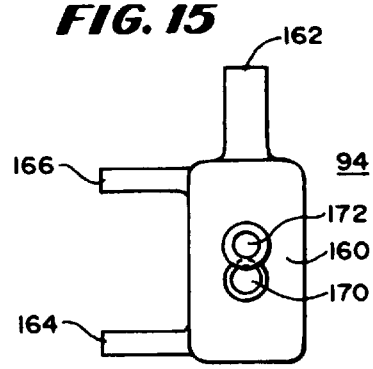
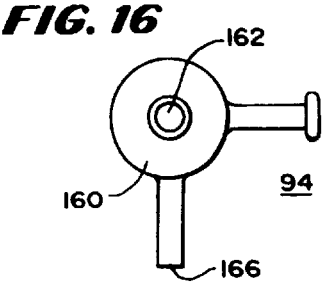
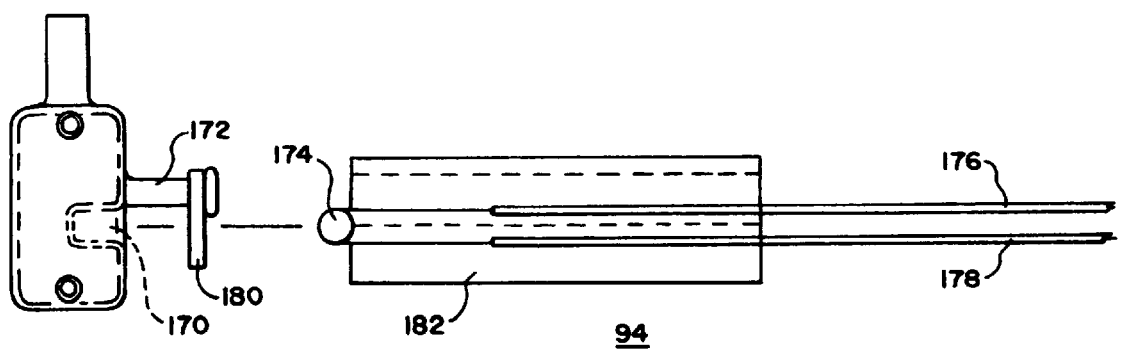

WATER IMPURITY ANALYZER

REFERENCE TO RELATED APPLICATIONS

This application is a divisional of U.S. application Ser. No. 08/634,007 filed Apr. 15, 1996, now U.S. Pat. No. 5,733,789 which is a divisional of U.S. application Ser. No. 08/386,699 filed Feb. 10, 1995, now U.S. Pat. No. 5,531,961 entitled WATER IMPURITY ANALYZER.

BACKGROUND OF THE INVENTION

This invention relates to apparatuses and methods for sensing impurities in water.

It is known to determine the amount of organic carbon in water being tested by oxidizing the organic carbon in a sample of water and measuring the amount of carbon dioxide obtained by such oxidation. One class of techniques and apparatus for measuring organic carbon are continuous in operation. In a continuous process, the organic carbon in water is oxidized as the water flows through an ultraviolet reactor and the amount of water flowing through the reactor is measured. The carbon dioxide formed by oxidizing the organic carbon in the measured water is also measured to provide an indication of the amount of organic carbon in a unit of water.

In a prior art continuous process for measuring the total organic content of water, each of the stages for oxidation of carbon has its own ultraviolet source and may have its own source of oxidizing agent and/or oxygen or there is a single ultraviolet source in a single stage.

The prior art apparatuses and techniques for measuring the total organic carbon content of water has several disadvantages, such as for example: (1) there is a tendency for some of the carbon dioxide to escape before it is collected and measured; (2) in those embodiments in which several ultraviolet light sources are used, the cost is high; and (3) it is difficult to obtain complete oxidation of the organic carbon.

SUMMARY OF THE INVENTION

Accordingly, it is an object of the invention to provide a novel apparatus and method for analyzing the organic carbon content of liquids.

It is a still further object of the invention to provide a novel technique for oxidizing carbon within liquids.

It is a still further object of the invention to provide a measuring technique and apparatus for total carbon analysis of water.

It is a still further object of the invention to provide a technique and apparatus for increasing the oxidation of carbon in minimum space and at minimum cost.

It is a still further object of the invention to provide a technique and apparatus that obtains a balance between the time necessary for mixing oxidizers with water containing organic compounds with the amount of time provided for ultraviolet irradiation and distance from the source of ultraviolet radiation so as to more effectively provide a total organic carbon measuring technique.

It is a still further object of the invention to provide a total organic carbon measuring technique which maximizes the recovery of gases formed by the oxidation of organic carbon in a liquid.

It is a still further object of the invention to provide a novel apparatus and method for determining the absence of liquid in a system.

It is a still further object of the invention to minimize the interaction between a plurality of reaction stages as the liquid and gas components rise through the ultraviolet reactor assembly.

It is a still further object of the invention to provide a novel method and apparatus for balancing the amount of oxygen, oxidizers and unreacted organic carbon to improve efficiency.

It is a still further object of the invention to provide an organic carbon analyzer that is easy to manufacture and maintain and permits easy variation in the construction of the column to reduce the cost and improve its ability to perform under different circumstances.

In accordance with the above and further objects of the invention, water is pumped through an apparatus for removing inorganic carbon and from there into a reactor where the water is mixed with an oxidizing agent and a carrier gas containing from zero percent to 100 percent oxygen such as air. The mixture is exposed to ultraviolet light and mixed in a plurality of residence time stages separated by stages in which it flows closely adjacent to a source of ultraviolet light to catalyze the oxidation of organic carbon.

The apparatus includes an elongated ultraviolet lamp which fits through the center of an elongated reactor chamber formed of a plurality of interconnectable parts. The mixture flows through a brief turbulent section into a residence chamber adjusted in length and width to accommodate the time needed for mixing and removal of gases, followed by flowing through a small curvilinear path through which the liquid flows in a helical path adjacent to and around the central ultraviolet lamp for intense radiation with ultraviolet light.

These two types of stages are repeated with the larger volume residence chambers providing time during which mixing reaction and separation of gas and water occurs. These residence chambers become shorter in length in a manner that balances the need for the separation and mixing time at slow linear rate of movements of liquid and with the helical sections providing fast linear movement along the helical path for intense irradiation and rapid movement near the lamp. This provides optimum combinations of irradiation, mixing reaction and separation of gas to provide total oxidation along the smallest unbroken path. The apparatus is economical because it includes a single ultraviolet lamp and provides complete capture of gases because of the unbroken path which obtains total oxidation.

From the above description, it can be understood that the carbon analyzing apparatus and technique of this invention has several advantages, such as: (1) it is economical to construct and includes only one ultraviolet lamp; (2) it reduces the loss of gases to be measured because it is a single element extending upwardly so as to collect all the desirable gas at the top of a single closed path; (3) it provides appropriate balances between mixing of oxidizing agents, carrier gas and sample, reaction time, irradiation and the appropriate intensities of turbulence suitable for the carbon content of the water; (4) it minimizes the interaction between the reaction stages as the liquid and gas components rise through the ultraviolet reactor assembly; (5) it permits the addition of reagents of intermediate points in the reaction; (6) it permits adjustment for other compounds such as sodium chloride that provide ions resulting in side reactions that compete with the carbon reaction; and (7) it permits ease of manufacture and maintenance and provides easy variation of the construction of the column to reduce the cost and improve its ability to perform under different circumstances.

SUMMARY OF THE DRAWINGS

The above noted and other features of the invention will be better understood from the following detailed description when considered with reference with the accompanying drawings, in which:

FIG. 4 is a simplified fragmentary perspective view partly broken away showing an embodiment of UV reactor;

FIG. 5 is a longitudinal sectional view of the reactor of FIG. 4;

FIG. 14 is a side elevational view of a liquid detector useful in the embodiment of FIGS. 1–13;

FIG. 15 is an end elevational view of the liquid detector of FIG. 14;

FIG. 16 is a top view of the liquid detector of FIG. 14; and

FIG. 17 is an exploded side elevational view of the liquid detector of FIG. 14 with a thermistor shown exploded away from it.

DETAILED DESCRIPTION

Figure 1:
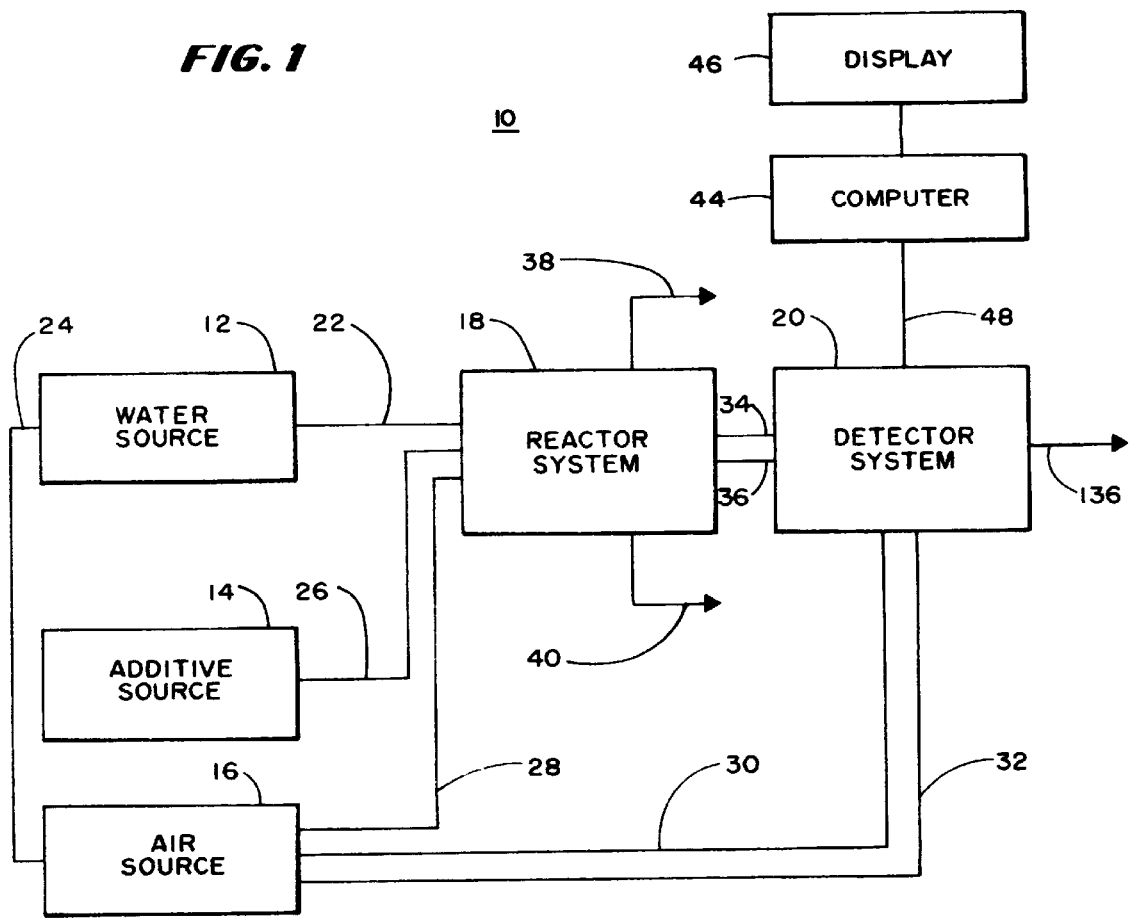
FIG. 1 is a block diagram of an embodiment of analyzer in accordance with the invention.

In FIG. 1, there is shown a block diagram of a continuous process, total-oxidation of carbon system 10 having a water sample source 12, an additive source 14, a carrier gas source 16 which may be air, a reactor system 18 and a detector system 20. In this system, a sample of water is pumped from a source of water 12 into the reactor system 18, mixed with additives from the source 14 and with air from the source 16 for mixing the additives and water. The organic carbon is oxidized in the reactor system 18 and measured in the detection system 20.

After processing, the water is pumped: (1) through the conduit 22 into the reactor system 18 which communicates between the source of water and the reactor system 18; (2) additives are pumped from the additive source 14 to the reactor system 18 through the conduit 26 which communicates with both of them; and (3) the reactor system 18 oxidizes the organic carbon within the sample of water and causes the resulting carbon gases to flow through a conduit 34 to the detection system 20 which detects and measures the amount of carbon gases resulting from the oxidation of organic carbon in the gas. This measurement is transmitted through a cable 48 to and utilized within a computer 44, which also controls the pumps and the like with which it communicates, to calculate the amount of organic carbon and transmit these values to the display 46 for printing and visualization.

The air source 16 supplies carrier gas, for example, air through the conduit 28 to the reactor 18 with which it communicates for oxidation of the organic carbon and also supplies air through the conduits 24 to the water supply system 12 and to the detector system 20 through the conduits 30 and 32 which communicates between them for uses to explained hereinafter. Purge gas from the detection system 20 is applied to the system vent in the reactor system 18 after serving as a counter-flow in the gas drier 52 (FIG. 2).

With this arrangement, the continuous process total oxidation of carbon system 10 supplies the sample water and oxidizing agent such as sodium persulfate or potassium persulfate to the reactor system together with a carrier gas such as air. This system mixes the carrier gas, oxidizing agent and water sample turbulently and supplies it through a large bulk flow section for slow linear movement during a residence time adequate for mixing them, and then, forces the water at the same volumetric flow rate but with very rapid linear velocity along a shallow helical path close to the UV source for exposure to UV light, heating and mixing at rapid velocity and close proximity to the ultraviolet light source. The reactor repeats this process until the total organic oxygen is oxidized as the liquid moves vertically upwardly along a single ultraviolet lamp to the top, where the carbon dioxide flows into a detector for detection, measuring and reporting.

Figure 2:
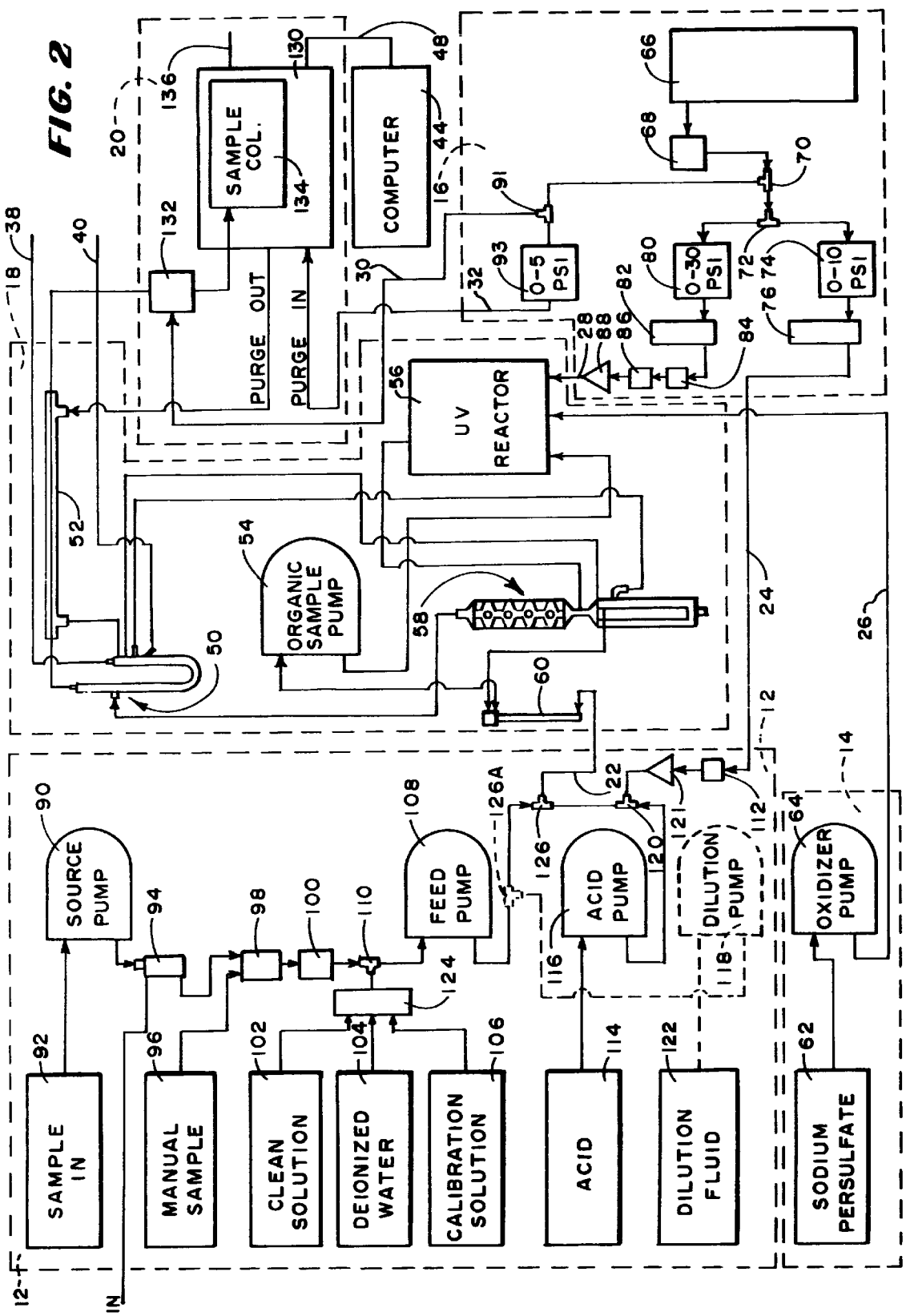
FIG. 2 is a schematic diagram of a system for total analysis of the organic carbon content of liquids in accordance with the invention.

In FIG. 2, there is shown a schematic diagram of the water source 12, the additive source 14, the air source 16, the reactor system 18 and the detector 20 connected together as described in connection with FIG. 1. As shown in FIG. 2, the reactor system 18 includes a first gas-liquid separator and condenser 58 serving also as a system liquid drain, a second gas-liquid separator 50, a gas drier 52 which serves as a gas-water vapor separator and an inorganic carbon sparge or scrubber 60 which also includes a third gas-liquid separator as its principal parts.

As shown in FIG. 2, the sample enters the reactor system through a conduit 22 and passes through the inorganic sparge 60 which removes inorganic carbon. Such inorganic carbon sparges are known in the art and the sparge 60 is not in itself part of the invention. The liquid, after being sparged is pumped by the organic sample pump 54 with which it communicates through conduits into the ultraviolet reactor 56 for reaction with an oxidizing agent. The gas/liquid mixture leaving the sparge 60 passes to the trap/condenser 58 where the gas/liquid mixture is then routed to the waste side of the gas separator 50. The gas separator 50 vents through line 38 and drains through line 40.

An oxidizer such as for example sodium persulfate is pumped through conduit 26 into the UV reactor from the source of oxidizer 62 and carrier gas is pumped into the ultraviolet reactor 56 from the carrier gas system 16. The gas flowing into the ultraviolet reactor 56 vigorously mixes the oxidizer and sample water, and in a series of stages, permits it to flow at a relatively low linear rate for mixing and then through a helical very rapidly moving path around and close to the UV lamp for reaction under the force of the catalyst ultraviolet light. These stages are sized to provide the proper amount of heavy exposure of UV light, mixing and separating of gas along a straight short vertical line for total oxidation of the organic carbon and removal of the total amount of carbon gases formed by oxidation. Thus, economical structure is used in a relatively short vertical height to obtain the total organic carbon.

The gas leaving the reactor 56 is passed through a conduit to the trap-condenser 58 at an upper location for further condensing of liquid and separation of gas. From the trap-condenser, the gas flows to the gas liquid separator 50 for further collection of liquid and from the top of the gas-liquid separator 50 through the Nafion tube gas drier 52. The Nafion drier includes an inner Nafion tube through which water vapor passes selectively in a manner known in the art and a counter flow of carrier gas between the inner tube and an outer tube to remove the water vapor to the gas-water separator 50 for draining through conduit 40.

From the gas drier 52, the carbon dioxide moves into the detector system 20. The separator 50 receives the counter flow containing gas and liquid vapore from the Nafion tube gas drier 52, a vent outlet below the inlet from the UV reactor of the trap/condenser 58 and from a still lower drain of the trap/condenser 58. It includes a system drain which causes the flow of liquid to conduit 40 for disposal when the liquid reaches a level lower than the top level of the separator 50, the top level of the separator 50 being utilized to permit the flow of gas to the Nafion tube gas drier 52.

To supply oxidizer to the UV reactor 56, the additive source 14 includes a source of sodium persulfate or potassium persulfate or other oxidizer 62 and an oxidizer pump 64 for pumping oxidizer into conduit 26 and from there to the UV reactor 56. The carrier gas source 16 includes a source of compressed gas 66, a carbon dioxide removal column 68, three tee-fittings 70, 72 and 90, three pressure regulators 74, 80 and 92, two flow meters 76 and 82, a flow switch 84, a capillary tube 86 and a check valve 88. The compressed gas 66 communicates through a conduit to an optional carbon dioxide removal column 68 which in turn communicates through the tee-fitting 70 with two other tee-connections 72 and 90. This supplies compressed gas for use in the entire continuous process total oxidation of carbon system 10. The tee-connection 90 supplies gas under pressure through one conduit 30 to the three-way valve 132 and supplies gas through the other outlet of the tee-fitting 90 to the zero to five pounds per square inch regulator 92 with a controlled flow rate of 250 cubic centimeters per minute through a second conduit 32 to the detection system 20 to purge the atmosphere surrounding the IR detector 130 of $CO_2$.

The other tee-connection 72 supplies gas: (1) through one conduit through the zero to 10 pounds per square inch regulator 74 and from there through the flow meter 76 through conduit 24 into the sample supplying system 12 for creating turbulence in the sparge 60; and (2) through a zero to 30 pounds per square inch pressure regulator 80, a flow meter 82, a flow switch 84, the capillary tube 86 and the check value 88 in that order to the ultraviolet reactor 56 to provide turbulence therein.

To supply sample to the ultraviolet reactor, the water sample source 12 includes as its principal parts a source of sample 92, a source pump 90 for pumping the sample, a loss of flow detection detector 94, a manual three-way valve 98, a source of manual sample 96, an electric two-way valve 100, a tee-fitting 110, a feed pump 108 and a second tee-fitting 126. These elements permit samples from the source 92 to be pumped by source pump 90 through the loss of flow detection detector 94, the manual three-way valve 98, the electric two-way valve 100, the tee-fitting 110, the feed pump 108 and the tee-fitting 126 to the conduit 22 for supplying the sample liquid and carrier gas to the inorganic carbon sparge 60.

The source pump 90 pumps liquid from a source through the loss-of-flow detector 94 and back to the source of liquid. The loss-of-flow detector 94 permits the turning off of the system in the absence of liquid sample flowing to avoid heat damage and also permits liquid sample to flow through it to the feed pump 108. The manual sample source 96 may provide a sample instead of the pump 90 from the manual three-way valve 98 by switching between a first position which is an off position or from a position communicating with loss of detection detector 94 to a position connected to the manual sample 96. The electric two-way valve provides over-all control for the flow through the tee-fitting 110 to the feed pump 108 for application through the tee-fitting 126 to the conduit 22.

To provide cleaning solution, de-ionizing water or calibrating solution, a three-into-one normally closed selector valve 124 has its inlets connected to the clean solution source 102, a source of de-ionized water 104 and a calibration solution 106. Its outlet, is connected to the tee-fitting 110 so that in combination with two-way valve 100, the feed pump may draw from sample, clean solution, de-ionized water or calibration solution through the tee-fitting 110. Similarly, acid may be supplied to the tee-fitting 120 from an acid source 114 to adjust the pH of the sample to a level sufficiently low to release carbon dioxide from the sample as a gas by the acid pump 116 for application to another inlet of the tee-fitting 126 and eventual application to the conduit 22. The tee-fitting 120 similarly can receive gas through conduit 24, the flow switch 112 and the check valve 121 for application through the tee-fitting 126 to the outlet conduit 22 from the air supply 16. A dilution fluid may be connected through the source of dilution fluid 122 and the dilution pump 118 through a tee-fitting 126A which is optionally included in series with the tee-fitting 126 so as to dilute liquid from the feed pump 108.

The detection system 20, includes an infrared detector 130 and a three-way valve 132. The infrared detector 130 includes a sample cell 134 to permit infrared detection and measurement of carbon dioxide within the sample cell 134 in a manner known in the art. Carbon dioxide after detection may be vented through the vent 136 and a signal applied to the computer 44 for analysis.

The carbon dioxide is applied from the gas drier 52 through the conduit 34 (FIG. 1) into the normally open position of the three-way valve 132. The three-way valve, besides having a normally open position, is also connected at the normally closed position to the conduit 30 from the source of gas at the tee-joint 90 to supply $CO_2$ free gas under pressure through the valve 132 and the sample cell 134 for use in calibrating the infrared detector 130. For purging purposes, the infrared detector 130 communicates with the gas tube drier 52, conduit 32 (FIG. 2) and receives a purging gas from the regulator 92.

Figure 3:
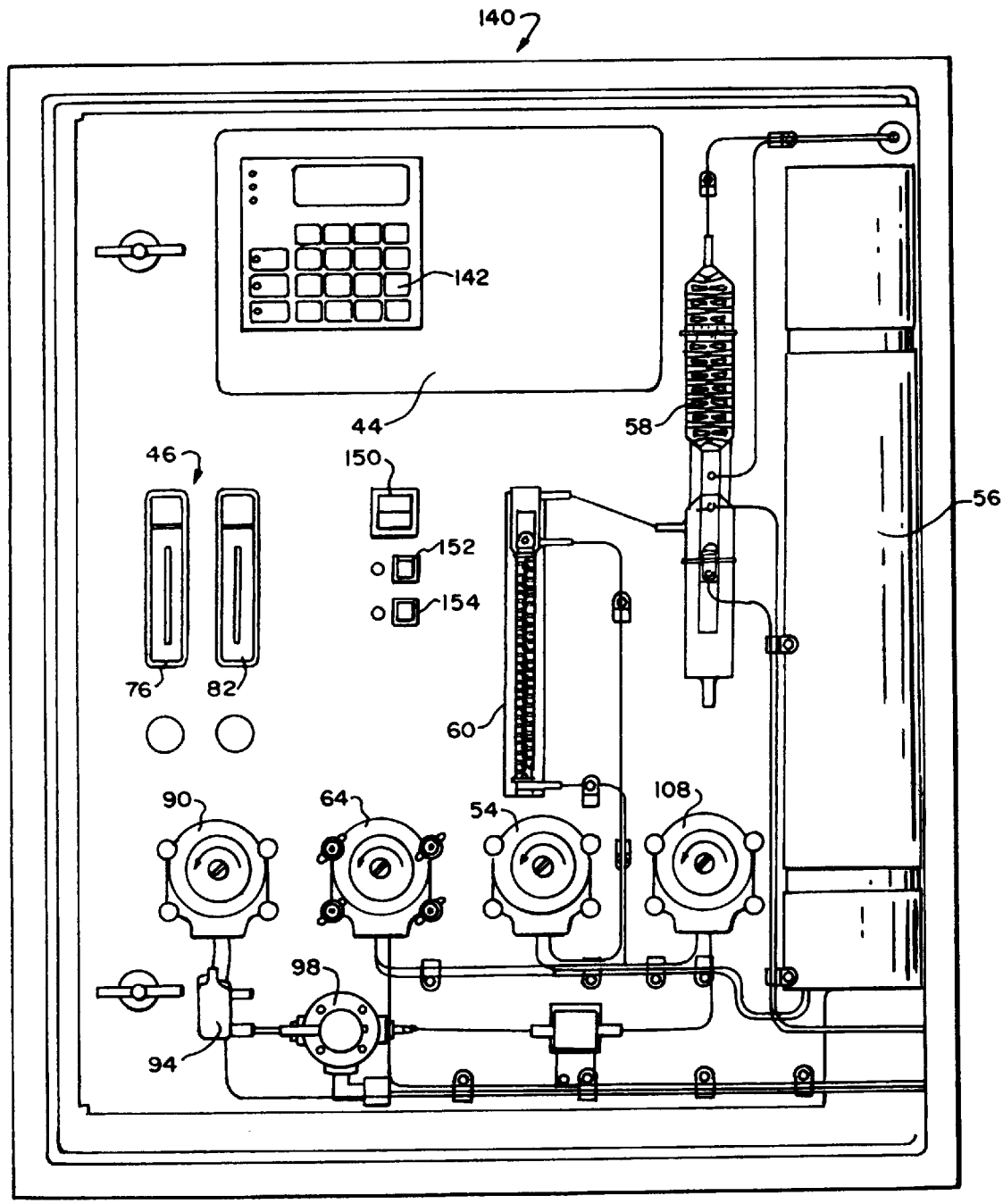
FIG. 3 is an elevational view of an instrument panel and instrument useful in the embodiment of FIGS. 1 and 2.

In FIG. 3, there is shown an elevational view of a control panel 140 showing the computer 44 with a keyboard 142, flowmeter displays shown at 76 and 82, the power switch 150, the ultraviolet reactor 56 (in a cabinet), power switches and indicators 152 and 154 for UV reactor and pump power respectively, the trap-condenser 58, the sparge 60, source selector switch 98 for selection of manual sample source or continuous sample source, the pumps 90, 64 (with 116 stacked behind it) 54 and 108 are all visibly shown on the front of the panel with the appropriate conduits connecting the ultraviolet reactor 56, the trap/condensor 58 and the scrubber 60. With this arrangement, convenient control through the computer panel are provided and the basic operation and indicators may be easily monitored.

In FIG. 4, there is shown a fragmentary broken away view of the UV reactor 56 having a generally cylindrical reactor bottom 154, a first reactor body 156, a second reactor body 158, a reactor top 160 and a ultraviolet lamp 150 having electrical conductors 152 connected to it. Several other reactor bodies may be included in this sequence.

With this arrangement, the reactor body 154 has a plurality of ports, with three being used in the preferred embodiment. One port is adapted to receive the sample and one port adapted to receive oxidizers, and one to receive carrier gas. The oxidizer may be potassium persulfate, sodium persulfate, ozone or others.

The three port openings are shown at 162, 164 and 166, spaced circumferentially around the end of the member to permit injection of liquids radially inwardly to a hollow center. At the bottom is an opening 168 internally threaded to receive a plug for sealing the bottom end or a mounting member for mounting the reactor and sealing the bottom end. At the top end is a shoulder ending in a reduced diameter externally threaded upwardly extending tube 170 adapted to receive an "O" ring and be threaded into the first body member 156 with an opening extending therethrough for the passage of liquid and to receive the ultraviolet lamp 150 which extends downwardly through the center for providing ultraviolet light as a catalyst to the liquid.

To provide for mixing of the fresh oxidizers with the high carbon water entering at the bottom, the first reactor body 156 includes a relatively large wide and long inner residence time chamber 172 having high volume between the walls of the first reactor body and the central ultraviolet lamp to provide relatively slow linear motion in stable condition during mixing with the high organic carbon liquid and high oxidizer concentrations. The size of the inner chamber is chosen in accordance with the volumetric rate of flow of this continuous reactor member and the expected organic carbon of the liquid to provide adequate mixing before reaching an end portion of the first body member.

Near the end of the first reactor body which is above the reactor bottom 154, is a narrowed section having internal grooves within it forming an upwardly extending helix as shown at 174 and similarly having external threads 176 for engaging internal threads in the second body member 158, the connecting sections being connected with "O" rings for sealing. An ultraviolet lamp fits relatively tightly against the walls so that the liquid moving upwardly in the ultraviolet reactor 56 in the narrowed section between the first reactor body 156 and the second reactor body 158 increases its linear speed to pass through the narrow helical passageway thus creating further turbulence, forcing the liquid closely against the ultraviolet lamp and increasing its path length along the helix to cause high intensity radiation with the catalytic ultraviolet light and mixing for reaction.

The liquid next passes into a second enlarged residence chamber in the second body member 158. This residence chamber may be smaller or larger than the lower chamber in the first reactor body 156. The diameter of residence chambers should be: (1) at least one and one-quarter times the diameter of the helix between residence chambers; and (2) at least two times the depth of said helical grooves.

The ability of the sections to be separated enables separate sizing depending on the expected carbon content of the liquid and permits more reactant or other additives to enter through separate ports into the second chamber if desired. More importantly the tailoring of the amount of oxidizer to match expected carbon content can be addressed anew as well as the residence time of moving through the larger chamber by changing the configuration, because the size of the residence chamber can be independently selected for insertion in the column. Any number of stages may be incorporated prior to the reactor top 160 which includes a final stage and the outlet ports for receiving reacted liquid and the separated carbon dioxide for measuring.

In FIG. 5 there is shown a longitudinal sectional view of a reactor 56 including the reactor bottom 154 showing one port 164 and the threaded bottom end 168 to receive a plug, the first reactor body 156 with its helical reaction section 174 and threaded narrow end 176, the second reactor body 158 and a third and fourth reactor bodies 178 and 180 connected together with the reactor top 160 being connected to the reactor body 180. The first, second and third reactor bodies are shown without a port but the fourth is shown having a radial port to supply additional reactants or air or to provide for the insertion of a temperature probe for monitoring reaction temperature. Any of the members may have a radial port for further treatment and the sizes of the sections may be adapted based on experience relating to the carbon content and the carrier gas passing through the residence chamber. At the top member 160 is a threaded opening 182 adapted to receive a nut for holding the UV lamp extending downwardly through the center of the reactor to a location adjacent to the plug that fits in the opening 168.

Generally, the residence chambers have a diameter: (1) of at least one and one-half times the diameter of the helix formed by the helical groves; and (2) at least four times the depth of the helical groove.

While in the preferred embodiment, a single ultraviolet lamp is utilized, multiple lamps could be utilized. However, it is desirable to utilize only one lamp for convenience in assembly and for reduction in cost since the ultraviolent lamps are a relatively expensive component. It is desirable to have a single upwardly extending column rather than broken columns since a single column reduces the opportunities for the escape of carbon dioxide gas prior to being measured.

Figure 6:
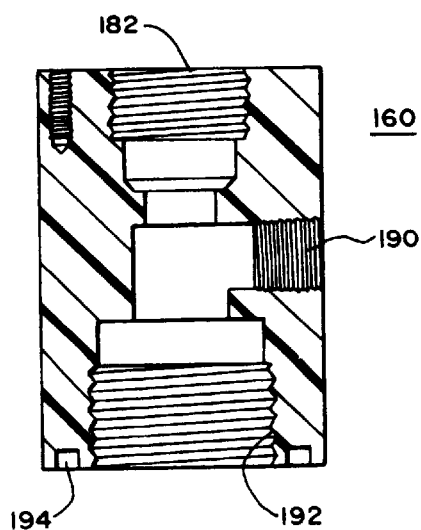
FIG. 6 is a longitudinal section view of a portion of the embodiment of FIG. 5.

In FIG. 6 there is shown a sectional view of a reactor top 160 having internal threads shown at 192 for connecting to the prior section a port 190 through which the liquid and gas leave and a threaded port 182 for receiving the ultraviolet lamp and ultraviolet lamp nut for inserting the ultraviolet lamp downwardly. The generally cylindrical tubular top in the preferred embodiment has approximately a two inch height with a 0.58 inch tapped port 182 in its top ending in a shoulder defining a circular opening extending downwardly 0.375 inches to the radial port 190. The overall outer diameter is approximately 1.5 inches. "O" rings are adapted to be positioned in the annular openings 194 for sealing the top member to the next lowest member.

Figure 8:
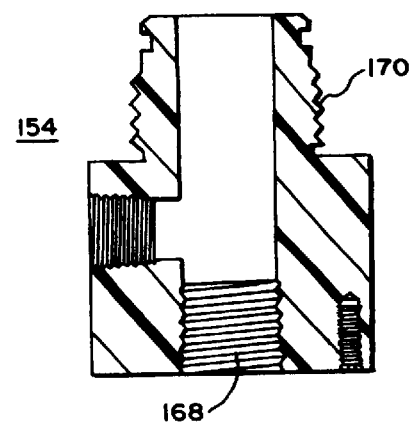
FIG. 8 is a sectional view of a portion of the embodiment of FIG. 5.
Figure 7:
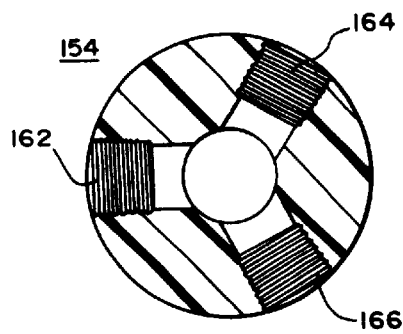
FIG. 7 is a transverse sectional view of a portion of the embodiment of FIG. 5.

In FIGS. 7 and 8 there are shown a transverse section and a longitudinal section respectively of the bottom member 154 showing the ports 162, 164 and 166 as well as the bottom member for receiving a plug shown at 168. The bottom reactor has a general height in the preferred embodiment of 1.9 inches, an outer circumference of 1.5 inches, with external 1–12 UNF-2B type threads 170 matching the internal threads of the first reactor body.

Figure 9:
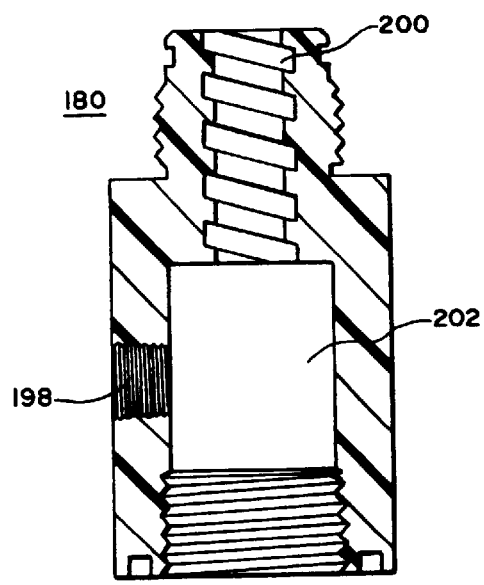
FIG. 9 is a longitudinal sectional view of still another portion of the embodiment of FIG. 5.

In FIG. 9, there is shown a reactor body having a port 198 similar to the fourth reactor body 180 in FIG. 5. Reactor bodies may not have ports or may have one or more ports and are selected for a reactor assembly in accordance with size and the need for a port depending on the organic carbon content of the liquid being tested and the design for measuring total organic carbon. The reactor body 180 has an outer dimension of 1.5 in this particular column to match the other members of the column and internal threads on one side to match the external threads on the prior member receiving the helical reaction section. Similarly, on its upper end it has external threads and an internal helix 200 for causing the liquid to rapidly flow along the helix in close proximity to the ultraviolet lamp.

The helix has a pitch of four with grooves $\frac{1}{8}$ inch wide separated by lands of $\frac{1}{8}$ inch that block the passage of the liquid between grooves to cause the liquid to flow along a helical path $\frac{1}{8}$ inch wide, a pitch of four and a depth of approximately $\frac{1}{8}$ inch. The helical path is approximately 1.19 inches in length along its vertical axis. The residence chamber is approximately 0.62 inches for this particular reaction body and it includes a threaded portion to provide a combined residence section of approximately 1.62 inches. It has an overall length of 2.81 inches and an inner diameter of the cavity of 0.875 inches which receives the ultraviolet lamp which has a diameter of 0.354 inches.

Figure 10:
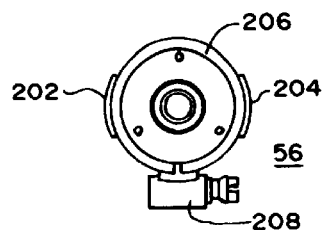
FIG. 10 is an end view of a fitting useful in the embodiment of FIG. 5.
Figure 11:
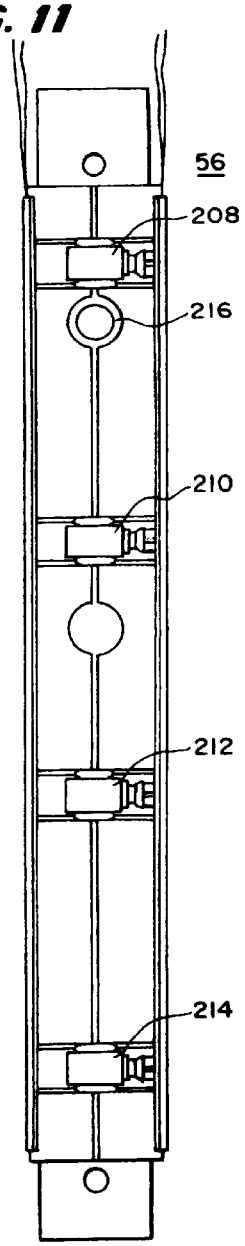
FIG. 11 is a side elevational view of an outer shell used for the UV reactor of FIG. 5.

In FIGS. 10 and 11 there are shown a top view and an elevational view of the reactor assembly 56 having heater strips 202 and 204 for controlling the temperature within the reaction chamber and mounted outside of a heat distribution tube 206. Clamps 208, 210, 212 and 214 are provided to compress the heat distribution tube 206 onto the assemblage of reactor sections shown in FIG. 5. A temperature probe 216 may be provided to measure the temperature within the reactor and thus provide feedback control to the temperature strips for maintaining the temperature at a desirable level. The feedback circuitry may be connected through the computer 44 (FIGS. 1 and 3).

Figure 12:
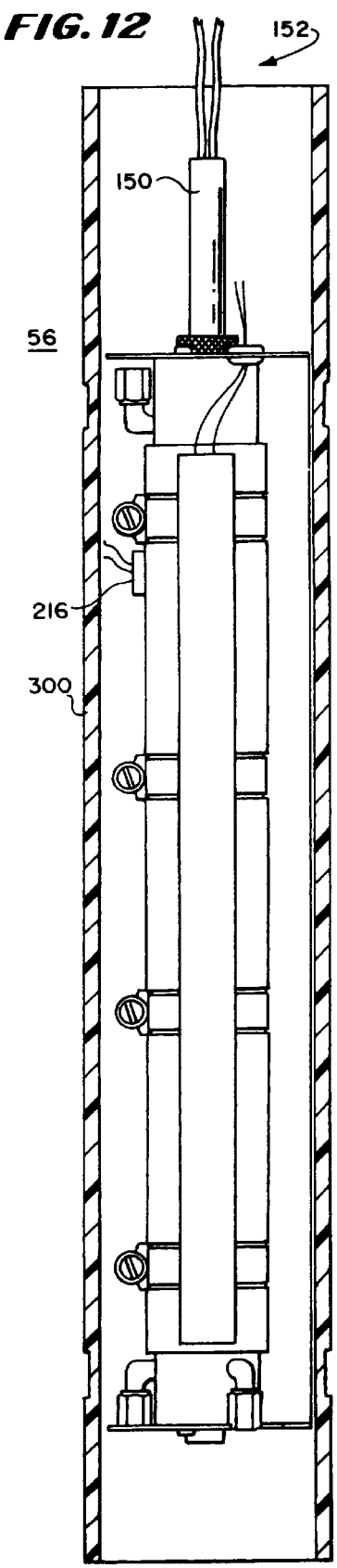
FIG. 12 is a sectional view of an outer casing of the embodiment of FIG. 5.

In FIG. 12, there is shown a $\frac{1}{8}$ inch thick tube 300 serving as a reactor shell for the purposes of providing protection and improving the appearance of the ultraviolet reactor. The upper and lower ends of the tube 300 are opened to receive conduits and electrical connections where necessary. The temperature probe 216 which is a thermistor is shown within the shell.

Figure 13:
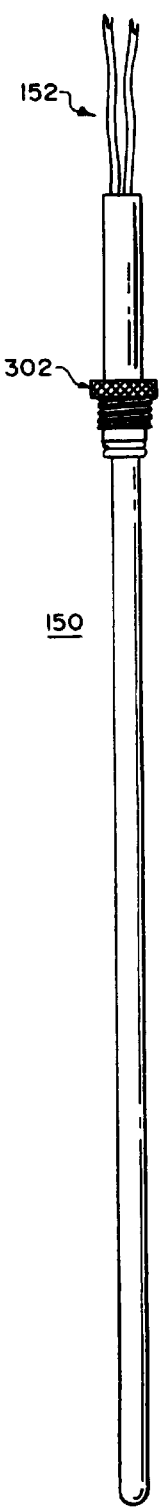
FIG. 13 is a side elevational view of an ultraviolet lamp useful in the embodiments in FIGS. 1–3.

In FIG. 13, there is shown an elevational view of the ultraviolet lamp 150 having an ultraviolet lamp nut 302 for threading into the opening 182 (FIG. 5) and extending downwardly through the reactor to provide ultraviolet light. In the preferred embodiment it is a low pressure mercury ultraviolet lamp having a lighted length of 15 $\frac{1}{4}$ inches, a tube outer diameter of 0.354 inches with a quartz glass envelope. It is commercially available and has a starting voltage of 3400 volts AC nominal and an operating voltage of 500 volts AC with a starting frequency of 10 KHz (kilohertz) and an operating frequency of 38 KHz. The operating current range is between 15 and 50 milliamperes.

In FIGS. 14, 15 and 16 there are shown a side elevational view, an end elevational view and a top view respectively of the loss of liquid detector 94 having a hollow body 160 and inlet port 162, an outlet port 164, and a fixed drain port 166. Sample flows through the inlet port 162 into the hollow body and out the outlet port 164 by the feed pump 108 (FIG. 3). The drain port 166 removes liquid which in the preferred embodiment varies between two and 26 cubic centimeters per minute depending upon the carbon content of the sample, and is drawn by gravity. The sample flowing through includes approximately 28 cubic centimeters per minute flowing into the loss of liquid detector and a portion out of the loss of liquid detector in a recirculated manner under the control of the source pump 90 (FIG. 2) and fixed drain 166.

As best shown in FIG. 14 and FIG. 15, the wall of the body 160 includes a cylindrical recess 170 (see FIG. 14 for its location) and a support post 172. As shown in the exploded view of FIG. 17, a thermistor 174 is adapted to fit into the opening 170 with electrical lead lines 176 and 178 extending therefore. The thermistor is held in place by the upstanding post 172, clamp 180 together with a shrink wrap packing 182 which hold the conductors 176 and 178 in place and adhesive placed inside recess 170.

In operation, if the sample liquid is interupted, the housing 160 heats up from the current through the thermistor and the thermistor 174 detects the temperature change. This detection results in a current change through conductors 176 and 178 which supplies a signal through the computer to shut down the unit. In the preferred embodiment, the insulation about the thermistor is such that it reaches its overheated condition within ten minutes without water cooling the thermistor and body but this time can be controlled by the amount of insulation. While liquid is flowing however, the flow of liquid through the body cools the body of the detector and thus maintains the temperature within a region suitable for operation.

On the other hand, if flow stops, liquid drains from the body 160 of the loss of liquid detector, the thermistor heats up and a signal is provided, preventing the overheating of the entire unit and possible damage.

From the above description, it can be understood that, the carbon analyzing apparatus and technique of this invention has several advantages, such as for example: (1) it is economical to construct and it may require only one ultraviolet lamp; (2) it reduces the amount of prematurely lost carbon dioxide because it may be formed as a single vertical column to permit collection of carbon dioxide at the top of the column; and (3) it provides relatively easy adjustment to maintain a balance between: (a) the time for mixing the oxidizing agents, carrier gas and samples; (b) the reaction time, (c) the amount and time of irradiation; and (d) the amount of oxidizing agent required.

More specifically, the use of separate residence reservoirs of relatively large size minimizes the interaction between the reaction stages as the liquid and gas components rise through the ultraviolet reactor assembly. This minimizes the possibility of liquid with organic carbon content that is high being mixed with only a small insufficient amount of unspent oxidizer. It provides a greater opportunity for balancing the amount of oxidizers and unreacted organic carbon to improve efficiency.

The separate residence time reservoirs also allow for addition of reagents of intermediate points in the reaction. This may be necessary when high carbon content in the liquid exhausts the oxygen in the reagents before the carbon is oxidized. Moreover, it permits adjustment for other compounds such as sodium chloride that provide ions resulting in side reaction that use up oxygen. Thus the reaction may be driven to completion not withstanding the presence of other compounds.

The use of a plurality of separate compartments which may be threaded together also permits ease of manufacture and maintenance and provides easy variety of the construction of the column so as to reduce the cost and improve its ability to perform under different circumstances.

While a preferred embodiment of the invention has been described in some detail, many modifications and variations in the embodiment are possible within the light of the above teachings. Therefore, it is to be understood, that within the scope of the appended claims, the invention may be practiced other than as specifically described.

What is claimed is:

1. A loss-of-liquid detector for a chemical reactor that detects the absence of sample fluid in a carbon-content of water measuring system comprising:

a carbon-content of water measuring system;

said carbon-content of water measuring system including sensing means; and means for cooling said sensing means with said sample fluid;

said sensing means including means for generating heat and sensing an increase in temperature wherein loss-of-fluid is detected.

2. A loss-of liquid detector for a chemical reactor in accordance with claim 1 in which said sensing means is a thermistor insulated to increase in temperature unless cooled by fluid.

* * * * *